(12) United States Patent
Jalkanen et al.

(10) Patent No.: US 8,119,651 B2
(45) Date of Patent: Feb. 21, 2012

(54) COMPOSITIONS USEFUL ESPECIALLY FOR TREATMENT OR PREVENTION OF METABOLIC SYNDROME

(75) Inventors: Sirpa Jalkanen, Piispanristi (FI); Marko Salmi, Turku (FI); Markku Jalkanen, Piispanristi (FI)

(73) Assignee: Biotie Therapies Corp., Turku (FI)

( * ) Notice: Subject to any disclaimer, the term of this patent is extended or adjusted under 35 U.S.C. 154(b) by 9 days.

(21) Appl. No.: 12/060,533

(22) Filed: Apr. 1, 2008

(65) Prior Publication Data
US 2008/0206313 A1   Aug. 28, 2008

Related U.S. Application Data

(63) Continuation-in-part of application No. 11/488,914, filed on Jul. 19, 2006, now abandoned, and a continuation-in-part of application No. PCT/FI2007/000206, filed on Aug. 22, 2007, which is a continuation-in-part of application No. PCT/FI2005/000035, filed on Jan. 19, 2005.

(60) Provisional application No. 60/578,896, filed on Jun. 14, 2004.

(51) Int. Cl.
A61K 31/51 (2006.01)
(52) U.S. Cl. ......................... 514/276; 514/866
(58) Field of Classification Search .................. None
See application file for complete search history.

(56) References Cited

U.S. PATENT DOCUMENTS

| | | | |
|---|---|---|---|
| 4,558,050 A | 12/1985 | Stacpoole | |
| 5,853,703 A | 12/1998 | Cerami et al. | |
| 2002/0173521 A1 | 11/2002 | Smith et al. | |
| 2002/0192842 A1 * | 12/2002 | Cerami et al. | |
| 2003/0125360 A1 | 7/2003 | Smith et al. | |
| 2005/0180956 A1 | 8/2005 | Conklin | |
| 2005/0182036 A1 * | 8/2005 | Kondo et al. | |
| 2006/0089316 A1 | 4/2006 | Brown et al. | |

FOREIGN PATENT DOCUMENTS

| | | |
|---|---|---|
| DE | 103 53 535 A1 | 6/2005 |
| EP | 0 511 587 A1 | 11/1992 |
| EP | 0 820 770 A2 | 1/1998 |
| EP | 0 820 771 A2 | 1/1998 |
| EP | 0 913 153 A1 | 5/1999 |
| JP | 1104142 A | 4/1989 |
| JP | 11192069 A | 7/1999 |
| JP | 2002193826 A | 7/2002 |
| WO | 93/23023 A1 | 11/1993 |
| WO | 02/02090 A2 | 1/2002 |
| WO | 02/02541 A2 | 1/2002 |
| WO | 02/38153 A1 | 5/2002 |
| WO | 03/006003 A1 | 1/2003 |
| WO | 2005072738 A1 | 8/2005 |
| WO | 2005095391 A1 | 10/2005 |

OTHER PUBLICATIONS

Metabolic Syndrome, American Heart Association, Copyright 2002, downloaded on Jan. 14, 2010 from "http://web.archive.org/web/20031003194644/http://www.americanheart.org/presenter.jhtml?identifier=4756", pp. 1-3 of 3.*
Patani et al., Chem. Rev., 1996, vol. 96, pp. 3147-3176.*
Database WPI/Thomson, JP2006008576, Dec. 28, 2007, 2 pages.
Takamizawa, Akira et al., "Studies on Pyrimidine Derivatives and Related Compounds, LXXVII, Reaction of Thiamine Analogues with Diethyl Benzoylphosphonate," Chemical & Pharmaceutical Bulletin, 1973, vol. 21, No. 4, pp. 770-784.
Thomas, M.C. et al., "The Role of AGEs and AGE Inhibitors in Diabetic Cardiovascular Disease," Current Drug Targets, 2005, vol. 6, No. 4, pp. 453-470.
Babaei-Jadidi, R. et al., "Prevention of Incipient Diabetic Nephropathy by High-Dose Thiamine and Benfotiamine," Diabetes, Aug. 2003, vol. 52, pp. 2110-2119.
Stepuro, I., "Thiamine and Vasculopathies," Prostaglandins, Leukotrienes and Essential Fatty Acids, 2005, vol. 72, pp. 115-127.
National Library of Medicine (NLM), file Medline, Medline accession No. 10629262, Avena, R. et al., "Thiamine (Vitamin B1) protects against glucose- and insulin-mediated proliferation of human infragenicular arterial smooth muscle cells," Annals of Vascular Surgery, Jan. 2000, vol. 14, No. 1, pp. 37-43 (1 page).
National Library of Medicine (NLM), file Medline, Medline accession No. 12882930, Babaei-Jadidi, R. et al., "Prevention of incipient diabetic nephropathy by high-dose thiamine and benfotiamine," Diabetes, Aug. 2003, vol. 52, No. 8, pp. 2110-2120 (1 page).
National Library of Medicine (NLM), file Medline, Medline accession No. 9794103, Bakker, S.J. et al., "The association of dietary fibres with glucose tolerance is partly explained by concomitant intake of thiamine: the Hoorn Study," Diabetologia, Oct. 1998, vol. 41, No. 10, pp. 1168-1175 (1 page).

(Continued)

Primary Examiner — James D Anderson
Assistant Examiner — Gregg Polansky
(74) Attorney, Agent, or Firm — Rothwell, Figg, Ernst & Manbeck P.C.

(57) ABSTRACT

This invention relates to a method for treatment or prevention of metabolic syndrome and diseases or conditions resulting therefrom in an individual, wherein an effective amount of an amine oxidase enzyme inhibitor is administered to said individual. In addition, the invention relates to a method for inhibiting an amine oxidase enzyme or for treatment or prevention of diseases or conditions benefiting from inhibition of an amine oxidase enzyme in an individual, wherein a vitamin B1, its derivative, its precursor or metabolite is administered to said individual. Finally, the invention relates to a food product comprising an amine oxidase enzyme inhibitor in combination with a foodstuff, a food additive comprising an amine oxidase enzyme inhibitor in combination with a liquid, solid or semisolid carrier.

5 Claims, 4 Drawing Sheets

OTHER PUBLICATIONS

Biosis, accession No. PREV200300110718, Dura, E. et al., "Determination of serum semicarbazide-sensitive amine oxidase activity in diabetic retinopathy, in Type 2 diabetes," Orvosi Hetilap, Nov. 2002, vol. 143, No. 47, pp. 2637-2644 (2 pages).

Accession No. PREV1998002328834, Ekblom, J., "Potential therapeutic value of drugs inhibiting semicarbazide-sensitive amine oxidase: Vascular cytoprotection in diabetes mellitus," Pharmaceutical Research, Feb. 1998, vol. 37, No. 2, pp. 87-92 (2 pages).

National Library of Medicine (NLM), NLM accession No. 10391401, "Elevated plasma semicarbazide-sensitive amine oxidase (SSAO) activity in Type 2 diabetes mellitus complicated by retinopathy," Diabetic Medicine: A Journal of the British Diabetic Association, Jun. 1999, vol. 16, No. 6, pp. 514-521 (1 page).

Search Strategy (CAN)(138:167951), Jain, A.K. et al., "Effect of high-glucose levels on protein oxidation in cultured lens cells, and in crystalline and albumin solution and its inhibition by vitamin B6 and N-acetylcysteine: its possible relevance to cataract formation in diabetes," Copyright 2004 American Chemical Society, (2 pages).

Database WPI/Derwent, accession No. 1979-36101B [19], "Thiamine derivs. exhibiting vitamin=B1 activity—and also antihypertensive and enzyme-inhibiting action," Takeda Chemical Industries Ltd., Abstract, (1 page).

Accession No. PREV200400113395, Kinemuchi, H. et al., "Selective inhibitors of membrane-bound semicarbazide-sensitive amine oxidase (SSAO) activity in mammalian tissues," Neurotoxicology (Amsterdam), Jan. 2004, Vol. 25, No. 1-2, pp. 325-335, (2 pages).

National Library of Medicine (NLM), NLM accession No. 12844520, Obrenovich, M. et al., "Vitamin B1 blocks damage caused by hyperglycemia," Science of Aging Knowledge Environment [electronic resource]: Sage KE, Mar. 2003, vol. 2003, No. 10, (1 page).

Search Strategy (CAN)(138:248286), Stitt, A. et al., "The AGE inhibitor pyridoxamine inhibits development of retinopathy in experimental diabetes," Copyright 2004 American Chemical Society, (2 pages).

National Library of Medicine (NLM), NLM accession No. 9389414, Yu, P.H. et al., "Aminoguanidine inhibits semicarbazide-sensitive amine oxidase activity: implications for advanced glycation and diabetic complications," Diabetologia, Nov. 1997, vol. 40, No. 11, pp. 1243-1250, (1 page).

Taylor, S.L. et al., "In vitro inhibition of rat intestinal histamine-metabolizing enzymes," Food Cosmet, Toxicol., 1979, vol. 17, No. 3, pp. 237-240.

Enrique-Tarancon, et al., "Role of Semicarbazide-sensitive Amine Oxidase on Glucose Transport and GLUT4 Recruitment to the Cell Surface in Adipose Cells," The Journal of Biological Chemistry, 273(14): 8025-8032 (Apr. 3, 1998).

Enrique-Tarancon, et al., "Substrates of semicarbazide-sensitive amine oxidase co-operate with vanadate to stimulate tyrosine phosphorylation of insulin-receptor-substrate proteins, phosphoinositide 3-kinase activity and GLUT4 translocation in adipose cells," Biochem Journal, 350: 171-180 (2000).

Zorzano, et al., "Semicarbazide-sensitive amine oxidase activity exerts insulin-like effects on glucose metabolism and insulin-signaling pathways in adipose cells," Biochimica et Biophysica Acta, 1647: 3-9 (2003).

Gokturk, et al., "Overexpression of Semicarbazide-Sensitive Amine Oxidase in Smooth Muscle Cells Leads to an Abnormal Structure of the Aortic Elastic Laminas," American Journal of Pathology, 163(5): 1921-1928 (Nov. 2003).

* cited by examiner

FP-1113, formula:

FIG. 3

COMPOSITIONS USEFUL ESPECIALLY FOR TREATMENT OR PREVENTION OF METABOLIC SYNDROME

CROSS-REFERENCE TO RELATED APPLICATIONS

The present application is a continuation-in-part of U.S. patent application Ser. No. 11/488,914 filed 19 Jul. 2006 and a continuation-in-part of International Patent Application No. PCT/FI2007/000206 filed 22 Aug. 2007. U.S. patent application Ser. No. 11/488,914 is a continuation-in-part of International Patent Application No. PCT/FI2005/000035 filed 19 Jan. 2005 which claims priority under 35 U.S.C. §119(d) to Finish patent application No. 20040136 filed 30 Jan. 2004 and which is related to and claims priority under 35 U.S.C. §119(e) to U.S. Provisional Patent Application No. 60/578, 896 filed on 14 Jun. 2004. International Patent Application No. PCT/FI2007/000206 claims priority under 35 U.S.C. §119(d) to Finish Patent Application No. 20060768 filed 28 Aug. 2006. Each application is incorporated herein by reference.

FIELD OF THE INVENTION

The present invention relates to the use of inhibitors of semicarbazide-sensitive amine oxidases (SSAO) for treatment or prevention of metabolic syndrome and diseases or conditions resulting therefrom. The invention also concerns the use of vitamin B1 or its derivatives, precursors or metabolites as SSAO-inhibitors, in particular for use in treatment or prevention of metabolic syndrome and diseases or conditions resulting therefrom. Furthermore, the invention concerns food products and food additives comprising an amine oxidase enzyme inhibitor as well as the use of said inhibitor as an additive to a foodstuff or as a dietary supplement.

BACKGROUND OF THE INVENTION

The publications and other materials used herein to illuminate the background of the invention, and in particular, cases to provide additional details respecting the practice, are incorporated by reference.

VAP-1 is a human endothelial cell adhesion molecule that has several unique properties that distinguish it from the other inflammation-related adhesion molecules. One of the most interesting features of VAP-1 is a catalytic extracellular domain which contains a monoamine oxidase activity (Smith, D. J., et al., J. Exp. Med. 188:17-27 (1998)).

The cloning and sequencing of the human VAP-1 cDNA revealed that it encodes a transmembrane protein with homology to a class of enzymes called the copper-containing amine oxidases (E.C. 1.4.3.6). Enzyme assays have shown that VAP-1 possesses a monoamine oxidase (MAO) activity which is present in the extracellular domain of the protein (Smith, D. J., et al., J. Exp. Med. 188:17-27 (1998)). Thus, VAP-1 is an ecto-enzyme. Analysis of the VAP-1 MAO activity showed that VAP-1 belongs to the class of membrane-bound MAO's termed semicarbazide-sensitive amine oxidases (SSAO). These are distinguished from the widely distributed mitochondrial MAO-A and B flavoproteins by amino acid sequence, cofactor, substrate specificity and sensitivity to certain inhibitors. However, certain substrates and inhibitors are common to both SSAO and MAO activities. The mammalian SSAO's can metabolize various monoamines produced endogenously or absorbed as dietary or xenobiotic substances. They act principally on primary aliphatic or aromatic monoamines such as methylamine or benzylamine (Lyles G. A., Int. J. Biochem. Cell Biol, 28:259-274 (1996)). Thus, VAP-1 located on the vascular endothelial cell surface can act on circulating primary monoamines with the following reaction pathway.

$RNH_2+O_2+H_2O \rightarrow RCHO+H_2O_2+NH_3$

The physiological substrates of VAP-1 SSAO in man have not been clearly identified. However, methylamine is a good substrate for VAP-1 SSAO. Methylamine is a product of various human biochemical pathways for the degradation of creatinine, sarcosine and adrenaline, and is found in various mammalian tissues and in blood. It can also be derived from the diet by gut bacterial degradation of dietary precursors. The concentration of methylamine in the blood can be increased in certain physiological and pathological situations such as diabetes. Another potential physiological substrate is aminoacetone.

VAP-1 SSAO activity has been proposed to be directly involved in the pathway of leukocyte adhesion to endothelial cells by a novel mechanism involving direct interaction with an amine substrate presented on a VAP-1 ligand expressed on the surface of a leukocyte (Salmi et al. Immunity, vol. 14, pp. 265-276 (2001)). This publication describes the direct involvement of VAP-1 SSAO activity in the process of adhesion of leukocytes to endothelium. Thus inhibitors of VAP-1 SSAO activity could be expected to reduce leukocyte adhesion in areas of inflammation and thereby reduce leukocyte trafficking into the inflamed region and therefore the inflammatory process itself.

In human clinical tissue samples expression of VAP-1 is induced at sites of inflammation. This increased level of VAP-1 can lead to increased production of $H_2O_2$ generated from the action of the VAP-1 SSAO extracellular domain on monoamines present in the blood. This generation of $H_2O_2$ in the localized environment of the endothelial cell could initiate other cellular events. $H_2O_2$ is a known signaling molecule that can upregulate other adhesion molecules and this increased adhesion molecule expression may lead to enhanced leukocyte trafficking into areas in which VAP-1 is expressed. It also may be that other products of the VAP-1 SSAO reaction could have biological effects also contributing to the inflammatory process. Thus the products of the VAP-1 SSAO activity may be involved in an escalation of the inflammatory process which could be blocked by specific SSAO inhibitors.

VAP-1 SSAO may be involved in a number of other pathological conditions associated with an increased level of circulating amine substrates of VAP-1 SSAO. The oxidative deamination of these substrates would lead to an increase in the level of toxic aldehydes and oxygen radicals in the local environment of the endothelial cell which could damage the cells leading to vascular damage. It has been proposed that the vasculopathies such as retinopathy, neuropathy and nephropathy could be treated with specific inhibitors of SSAO activity.

Takahashi, H, et al., Yakugaku Zasshi 101(12):1154-1156 (1981) report the synthesis of a number of N-alkylaminoephedrines, including N-(isopropylideneamino)-ephedrine or R,S-(+)-(2-hydroxy-1-methyl-2-phenylethyl)methylhydrazone-2-propanone. These hydrazone compounds were synthesized to evaluate their effect on the bronchial musculature and were found not to exhibit any significant activity.

Grifantini, M., et al., Farmaco, Ed. Sci. 23(3):197-203 (1968), report the synthesis of several alkyl- and acyl-derivatives of N-amino-1-ephedrine and N-amino-d-pseudoephedrine having antidepressant and monoamine oxidase inhibitory properties.

Jeffrey O'Sullivan et al., Biochimica et Biophysica Acta 1647 (2003) 367-371 report the inhibition of semicarbazide-sensitive amine oxidases by certain aminohexoses, namely glucosamine, galactosamine and mannosamine.

The international patent publications WO 02/020290 and WO 03/006003 disclose certain hydrazino compounds useful as specific VAP-1 SSAO inhibitors that modulate VAP-1 activity. These compounds are described as useful for the treatment of acute and chronic inflammatory conditions or diseases as well as diseases related to carbohydrate metabolism, aberrations in adipocyte differentiation or function and smooth muscle cell function, and various vascular diseases.

OBJECTS AND SUMMARY OF THE INVENTION

Based on a recent study to be referred hereinafter, the inventors have found that transgenic mice overexpressing vascular adhesion protein-1 (VAP-1), chronically challenged with an additional SSAO substrate or an atherogenic diet, showed an increased glucose uptake, compared to non-transgenic mice. An end product of the SSAO metabolism, hydrogen peroxide, can produce insulin-like effects enhancing glucose uptake. Based on the findings, the inventors propose that amine oxidase enzyme activity is increased in metabolic syndrome as an attempt to regulate blood glucose levels, and that complications resulting from metabolic syndrome are subsequently promoted as a consequence of the enhanced enzyme activity.

According to one aspect, this invention concerns the use of an amine oxidase enzyme inhibitor in the treatment or prevention of metabolic syndrome and diseases or conditions resulting therefrom.

According to another aspect, the invention concerns the use of vitamin B1 or a derivative or metabolite thereof or precursor therefore as an amine oxidase enzyme inhibitor.

According to third aspect, the invention concerns a food product comprising an amine oxidase enzyme inhibitor in combination with a foodstuff, wherein said amine oxidase enzyme inhibitor is a vitamin B1 derivative or vitamin B1 precursor.

According to a fourth aspect, the invention concerns a food additive comprising an amine oxidase enzyme inhibitor, especially a vitamin B1 derivative or vitamin B1 precursor, in combination with a liquid, solid or semisolid carrier.

According to a fifth aspect, the invention concerns the use of an amine oxidase enzyme inhibitor as an additive to a foodstuff.

According to a sixth aspect, the invention concerns vitamin B1, a vitamin B1 derivative or a vitamin B1 precursor for use as an amine oxidase enzyme inhibitor in a non-diabetic individual, especially for use in the treatment or prevention of metabolic syndrome and diseases or conditions resulting therefrom.

According to a seventh aspect, the invention concerns a method for treatment or prevention of diseases or conditions in a non-diabetic individual, benefiting from inhibition of an amine oxidase enzyme, particularly for treating or preventing metabolic syndrome and diseases or conditions resulting therefrom in a non-diabetic individual, said method comprising administering to the individual an effective amount of vitamin B1, a vitamin B1 derivative or a vitamin B1 precursor.

According to a eighth aspect, the invention concerns novel vitamin B1 derivatives in which the pyrimidine ring of thiamine is replaced by another aromatic group.

According to a ninth aspect, the invention concerns vitamin B1 derivatives in which the pyrimidine ring of thiamine is replaced by another aromatic group, for use in therapy.

According to an tenth aspect, the invention concerns vitamin B1 derivatives in which the pyrimidine ring of thiamine is replaced by another aromatic group, for use as amine oxidase enzyme inhibitors, especially for use in the treatment or prevention of metabolic syndrome and diseases or conditions resulting therefrom.

BRIEF DESCRIPTION OF THE FIGURES

FIGS. 1A-1D show human VAP-1 over-expression and methylamine supplementation enhance glucose tolerance. The increases in blood glucose over fasting blood glucose levels at 30, 60, 90, and 120 minutes after glucose challenge (2.0 g IP glucose/kg body weight) are expressed as mean±SEM.

FIGS. 2A and 2B show advanced glycation end product (AGE) formation.

DETAILED DESCRIPTION OF THE INVENTION

The term "metabolic syndrome" shall be understood to include the following abnormalities: central obesity, dyslipidemia including particularly hypertriglyceridemia, low HDL cholesterol, small dense LDL particles and postpranial lipemia; glucose intolerance such as impaired fasting glucose; insulin resistance and hypertension.

It shall be stressed that "metabolic syndrome" is not the same as diabetics. Metabolic syndrome is considered as accumulation of conditions potentially leading to coronary diseases. Such conditions are middle body obesity, hypertriglyceridemia, low high density cholesterol, high blood pressure and increased fasting blood glucose. The individuals affected by metabolic syndrome do not need to have diabetes.

The term "complications related to metabolic syndrome" shall be understood to include any disease or disorder resulting from said syndrome. Such diseases are particularly different types of microalbuminuria; impaired fibrinolysis and increased coagulability including elevated plasminogen activator inhibitor-1 (PAI-1), elevated fibrinogen and increased levels of von Willebrand factor; signs of chronic inflammation such as elevated C-reactive protein (CRP); endothelial dysfunction such as impaired endothelium-dependent vasodilation; fatty liver disease and microangiopathy. As non-limiting examples of specific diseases and disorders can be mentioned atherosclerosis, vascular retinopathies, retinopathy, glomerulosclerosis, nephropathy, nephrotic syndrome, polyneuropathy, mononeuropathies, autonomic neuropathy, glaucoma, grey cataract, foot ulcers, joint problems, and increased risk of infection.

According to International Diabetes Federation, a person is suffering from metabolic syndrome in case the following criteria are fulfilled:

Central obesity; waist circumference >94 cm (male) and >80 cm (female) and

Two of the following:
1. Hypertriglyceridemia; triglycerides >1.7 mmol/l
2. Low HDL cholesterol; <1.03 mmol/l (male) and <1.29 mmol/l (female)
3. Hypertension; blood pressure >130/85 and/or medication
4. Fasting plasma glucose >5.6 mmol/l or type 2 diabetes For more information, see Duodecim 2005; 121:1521-30.

The term "prevention" shall be understood to include complete prevention, prophylaxis, as well as lowering the individual's risk of falling ill with said disease or condition. The term shall also be understood to include alleviation of symptoms already developed.

The term "treatment" or "treating" shall be understood to include complete curing of a disease or condition, as well as amelioration or alleviation of said disease or condition.

The term "individual" refers to a human or animal subject.

The term "amine oxidase enzyme inhibitor" shall here be understood to cover any known or still undiscovered compound having this activity. It shall also be understood to cover any isomer, isomeric mixture, and any pharmaceutically or physiologically acceptable salt of such a compound.

A particularly preferred amine oxidase enzyme inhibitor is a VAP-1 inhibitor.

The amine oxidase enzyme inhibitor is especially useful in the treatment or prevention of complications derived from metabolic syndromes.

When used in a pharmaceutical composition for use in prevention or treatment of metabolic syndrome and diseases or conditions resulting therefrom, the amine oxidase enzyme inhibitor, its isomer, isomer mixture or its pharmaceutically acceptable salt can be administered by various routes. For example, administration can be by parenteral, subcutaneous, intravenous, intraarticular, intrathecal, intramuscular, intraperitoneal, or intradermal injections, or by transdermal, buccal, oromucosal, ocular routes or via inhalation. Alternatively, or concurrently, administration can be by the oral route. Particularly preferred is oral administration. Suitable oral formulations include e.g. conventional or slow-release tablets and gelatine capsules.

The required dosage of the compounds will vary with the particular disease or condition being treated, the severity of the condition, the duration of the treatment, the administration route and the specific compound being employed.

Thus, a typical dose is in the dosage range of about 0.1 microgram/kg to about 300 mg/kg, preferably between 1.0 microgram/kg to 10 mg/kg body weight. Compounds of the present invention may be administered in a single daily dose, or the total daily dosage may be administered in divided doses of two, three or four times daily.

The term "foodstuff" shall be understood as any edible ingredient of plant or animal origin or synthetically prepared, which is useful as an energy supplier to the mammalian body. It can thus include carbohydrates, proteins or fats or their mixtures and/or compositions with other ingredients, especially with water. The foodstuff can be a basic foodstuff such as vegetables, cereals, flour, milk, meat, egg, butter, margarine, etc. As foodstuff shall also be considered any finished compositions, such as bread, cakes, yogurt and other milk products, finished meals etc.

The food product according to this invention is any food product, but especially a functional food, a nutritional supplement, a nutrient, a pharmafood, a nutraceutical, a health food, or a designer food. A suitable concentration of the amine oxidase enzyme inhibitor depends on the particular inhibitor used as well on the food product in question.

The functional food according to this invention can be any foodstuff supplemented with an amine oxidase enzyme inhibitor. As non-limiting examples can be mentioned butter, margarine, biscuits, bread, cake, candy, confectionery, yogurt or an other fermented milk product, or cereal such as muesli.

As a particularly useful foodstuff can be mentioned rye and various rye based products.

Although the amine oxidase enzyme inhibitor in principle could be added as such to a food manufacturing process, it may be preferable in order to achieve exact dosing to first mix the inhibitor with a carrier before it is added to the food manufacturing process.

This invention concerns also a food additive comprising an amine oxidase enzyme inhibitor in combination with a liquid, solid or semisolid carrier. The carrier can be any edible, non-toxic solid, semi-solid or liquid carrier acceptable for use in food and suitable to be admixed with the amine oxidase enzyme inhibitor without affecting the properties of the inhibitor. The role of the carrier is mainly to make the exact dosage of amine oxidase enzyme inhibitor easier. The suitable concentration of the inhibitor in the food additive depends on the inhibitor in question and the proposed use of the food additive.

The food additive according to this invention can according to one alternative be used by food industry in processing various food products comprising a foodstuff supplemented with an amine oxidase enzyme inhibitor. For this purpose the food additive it is conveniently packed in a package suitable for industrial use in the addition of the additive in the food manufacturing process.

According to another alternative, the food additive can be directly used by the consumer, e.g. by dosing a certain amount of food additive onto a meal to be in-taken. In this alternative it could be preferable to equip the package with means giving guidance on a proper amount and restricting overdosing by mistake.

According to a particularly preferred embodiment, the food additive is in the form of a unit dosage to be used as a dietary supplement. Thus, the wording "food additive" shall not be interpreted narrowly to mean that the food additive always first must be added to a foodstuff before the intake by the consumer. A dietary supplement can be in-taken directly without first mixing it with a foodstuff. The dietary supplement can be in-taken in connection with a meal, but it could alternatively be in-taken between two meals.

A particularly useful amine oxidase inhibitor is vitamin B1, its derivative, precursor or metabolite. The term "derivative" shall here be understood to cover any vitamin B1 derivative, especially compounds having SSAO inhibiting activity. Especially preferred are those having no angiotensive converting enzyme-inhibiting action or quininase inhibiting action. Particularly preferred vitamin B1 derivatives are compounds in which the pyrimidine ring of thiamine is replaced by another aromatic group, for example but not restricted to, a phenyl group, which may be substituted or unsubstituted. As a particularly preferred compound can be mentioned 3-(2-aminobenzyl)-5-(2-hydroxyethyl)-4-methyl-thiazolium chloride hydrochloride, which has the structure formula shown in FIG. 3, and which in the tests appeared to be a stronger amine oxidase enzyme inhibitor than thiamine.

A particularly preferable precursor (or prodrug) for vitamin B1 is the compound benfotiamine, which is fat soluble.

Typical dosage forms for a dietary supplement comprising an amine oxidase enzyme inhibitor include, but are not limited to, oral dosage forms such as powders, granules, capsules, tablets, caplets, lozenges, liquids, elixirs, emulsions and suspensions. All such dosage forms may include conventional carriers, diluents, excipients, binders and additives known to those skilled in the art.

Typical solid carriers include polysaccharides such as lactose, sucrose, gelatin, agar, while liquid carriers include aqueous solutions of salts, polysaccharides, complexing agents, surfactants, syrups, vegetable oils such as peanut oil or olive oil, and certain alcohols. However, any acceptable solid, semisolid or liquid carrier can be used in the food additive according to the invention. However, a food additive formulation being a mixture of only the active agent and plain water is expected to be less feasible.

Although the food product and food additive described above are particularly useful for person suffering from or at risk of metabolic syndrome, these products may have valuable health promoting effects also in other individuals, particularly in individuals suffering from or being at risk of diseases or conditions caused by increased amine oxidase enzyme activity. As examples of such groups of diseases or conditions can be mentioned inflammatory diseases or conditions; diseases related to aberrations in adipocyte differentiation or function or smooth muscle cell function and vascular diseases.

As examples of such inflammatory diseases or conditions can be mentioned connective tissue inflammatory diseases or conditions such as ankylosing spondylitis, Reiter's syndrome, psoriatic arthritis, osteoarthritis or degenerative joint disease, rheumatoid arthritis, Sjögren's syndrome, Bechet's syndrome, relapsing polychondritis, systemic lupus erythematosus, discoid lupus erythematosus, systemic sclerosis, eosinophilic fasciitis, polymyositis and dermatomyositis, polymyalgia rheumatica, vasculitis, temporal arteritis, polyarterisis nodosa, Wegner's granulamatosis, mixed connective tissue disease, and juvenile rheumatoid arthritis, gastrointestinal inflammatory diseases or conditions, such as Crohn's disease, ulcerative colitis, irritable bowel syndrome (spastic colon), fibrotic conditions of the liver, inflammation of the oral mucosa (stomatitis), and recurrent aphtous stomatitis, central nervous system inflammatory diseases or conditions, such as multiple sclerosis, Alzheimer's disease, and ischemia-reperfusion injury associated with ischemic stroke, pulmonary inflammatory diseases or conditions, such as asthma, chronic obstructive pulmonary disease, or adult respiratory distress syndrome, skin inflammatory diseases or conditions, such as contact dermatitis, atopic dermatitis, psoriasis, pityriasis rosea, lichen planus, and pityriasis rubra pilaris, inflammatory conditions related to tissue trauma or resulting from organ transplantations or other surgical operations.

As examples of diseases relating to aberrations in adipocyte differentiation or function or smooth muscle cell function can be mentioned atherosclerosis and obesity.

As examples of vascular diseases can be mentioned atheromatous ateriosclerosis, nonatheromateous ateriosclerosis, ischemic heart disease, peripheral aterial occlusion, thromboangiitis obliterans (Buerger's disease), or Raynaud's disease and phenomenon.

The invention will be illuminated by the following non-restrictive Experimental Section.

EXPERIMENTAL SECTION

Specific Aims

This work investigates the in vivo significance of elevated semicarbazide sensitive amine oxidation (SSAO). To investigate the insulin mimicking capacity of VAP-1 activity and to test its ability to cause and/or exacerbate vascular complications we overexpressed VAP-1, an endothelial cell surface and soluble molecule possessing SSAO activity, in transgenic mice and then chronically challenged the mice for 15 months with additional SSAO substrate or an atherogenic diet.

Principle Findings

1) Chronic Human VAP-1 Overexpression Promotes Obesity.

Despite a decreased caloric intake the transgenic mice had increased weight, body mass index (BMI), and subcutaneous abdominal and epididymal white adipose tissue (WAT) deposits when compared to controls.

2) Blood Glucose is Regulated by VAP-1 Activity.

Figure 1A:
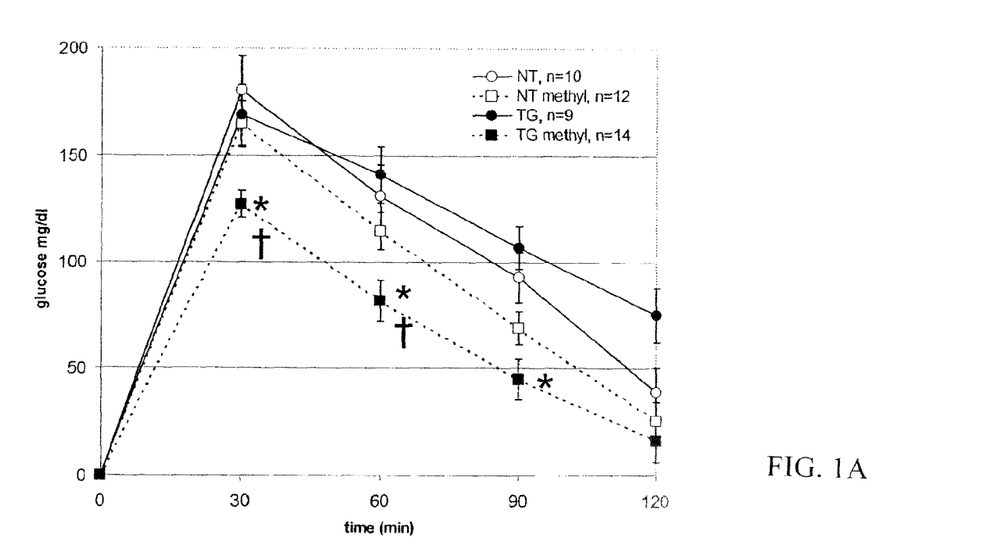
FIG. 1A: Glucose challenge of 26 week old non-transgenic (open symbols) and mTIEhVAP-1 transgenic mice (filled symbols) with normal tap water (solid lines) or with methylamine supplemented water (dashed lines).
Figure 1B:
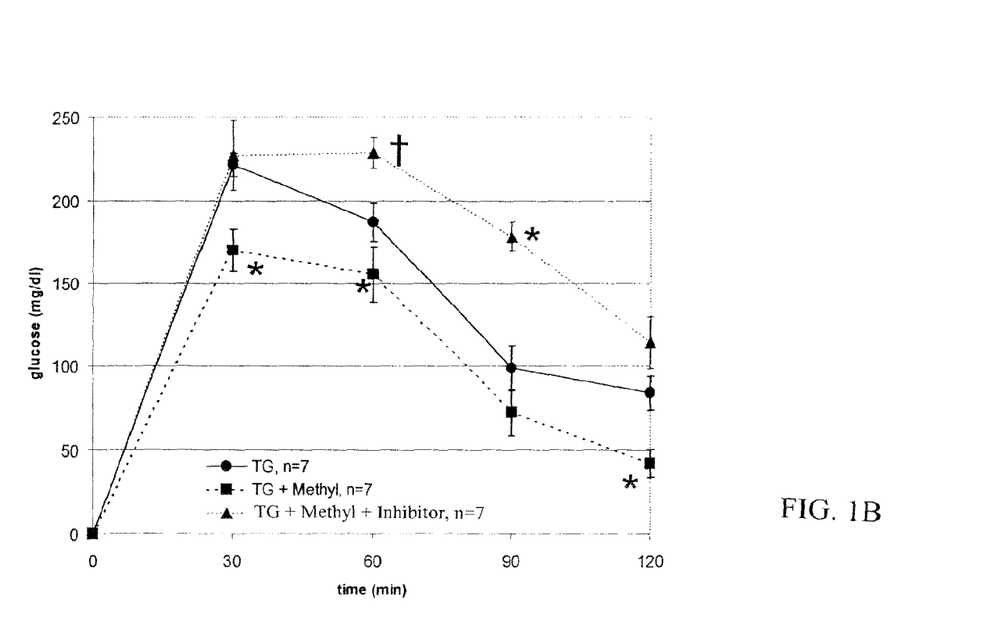
FIG. 1B: Glucose challenge of 10-12 week old transgenic mice with normal tap water (solid line) followed by 16 days of treatment with methylamine supplemented water (squares and dashed lines), and methylamine supplemented water as well as SSAO inhibitor injections (triangles and dashed lines).
Figure 1C:
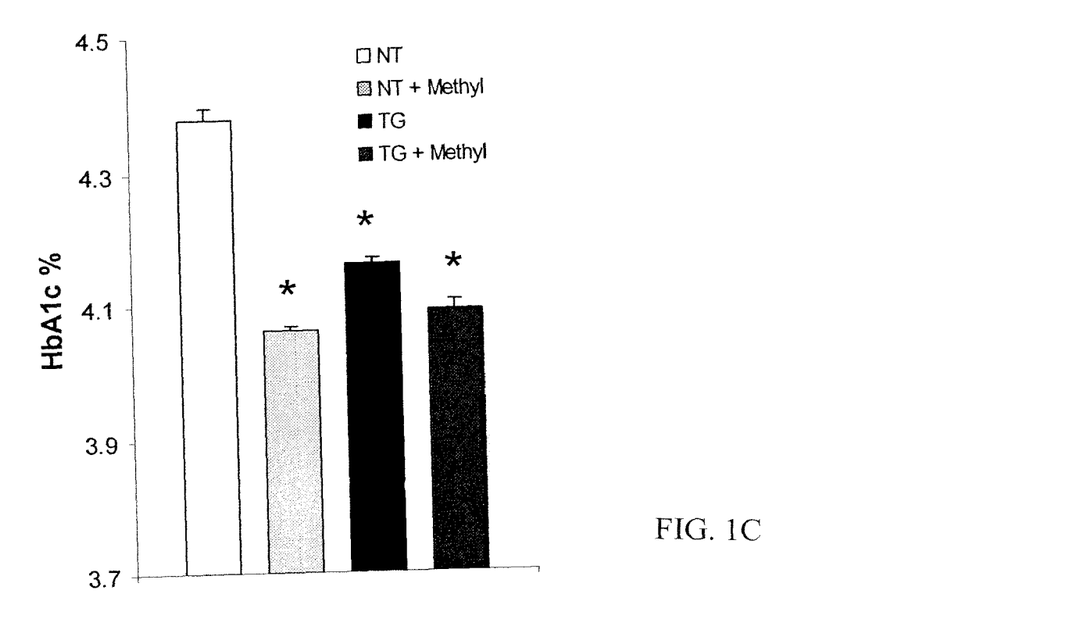
FIG. 1C: The mean±SEM percent of glycosylated hemoglobin (HbAlc) was determined from the blood of fasted, 57-59 week old non-transgenic (white bars) and transgenic (black bars) mice with (gray strips) or without oral methylamine supplementation.
Figure 1D:
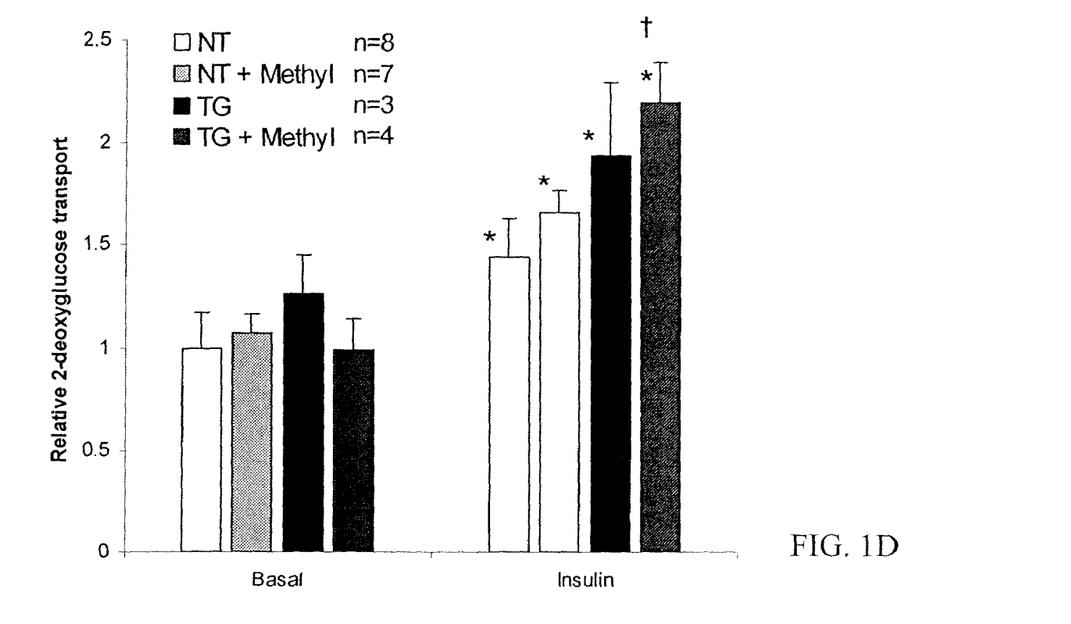
FIG. 1D: Glucose transport activity of muscles from non-transgenic and mTIEhVAP-1 transgenic mice.

The combination of the transgene and methylamine enhanced glucose uptake when the mice were fasted and challenged with glucose (FIG. 1A). This increase could be blocked with a small molecule inhibitor of SSAO (FIG. 1B). The fasting glucose levels were also decreased by the transgene and HbA1c levels were decreased by the transgene and/or methylamine supplementation (FIG. 1C). This amelioration of plasma glucose and glucose tolerance can be explained, at least in part, by improved insulin responsiveness of the skeletal muscle (FIG. 1D).

3) VAP-1 Overexpression Increases Advanced Glycation End Product (AGE) Formation.

Figure 2A:
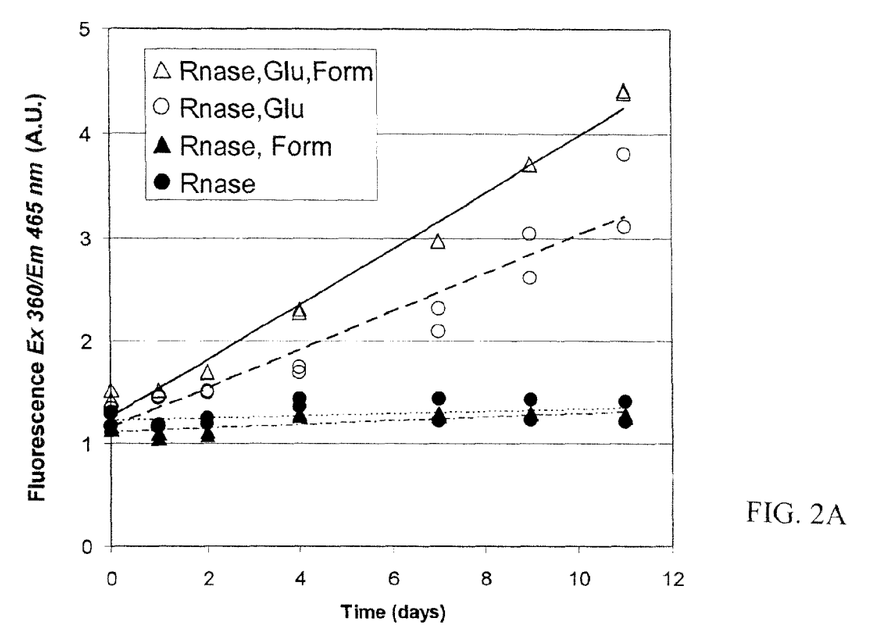
FIG. 2A: The SSAO reaction product, formaldehyde, promotes AGE formation in vitro.
Figure 2B:
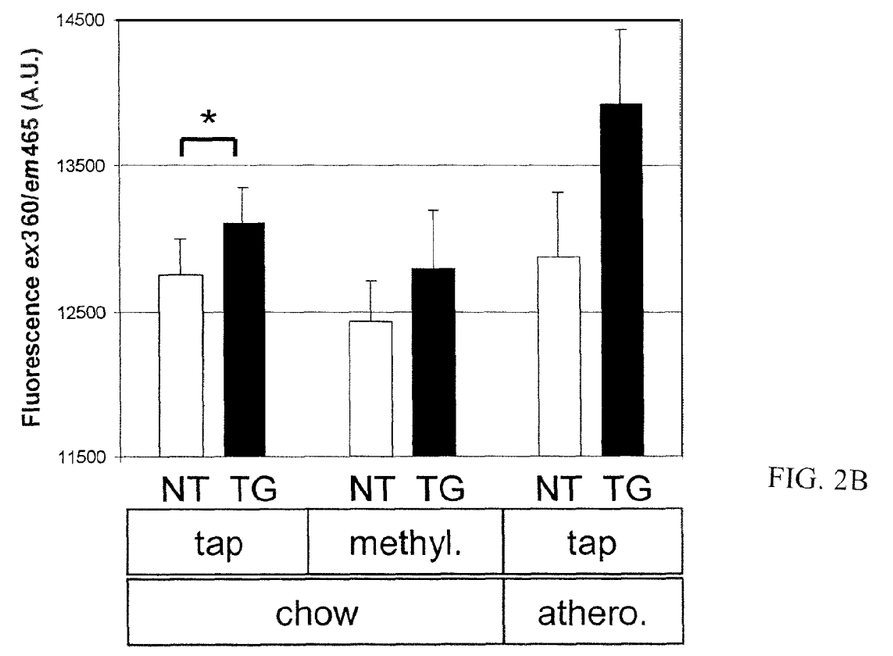
FIG. 2B: The mTIEhVAP-1 transgene increases AGE-peptide levels in the sera of 64 week old mice.

AGE-peptide levels were measured by fluorescence spectroscopy in the sera of the 64 week old mice. The level of AGE-specific fluorescence (ex 360, em 465) was increased in the presence of the transgene (FIG. 2). The fluorescence from tryptophan (ex 280, em 333), an internal standard of protein concentration, did not significantly vary between the groups.

4) Methylamine Supplementation Promotes Hypertension.

Systolic arterial blood pressure and heart rate were measured in all of the groups using the tail cuff method. Methylamine supplementation significantly elevated blood pressure but did not affect heart rate. A trend for elevated blood pressure was also found with the transgene alone.

5) Methylamine Supplementation and the mTIEhVAP-1 Transgene Modify the Progression of Atherosclerosis.

The percentage of aorta surface area positive for Oil Red O staining was determined for the mice in each group. Methylamine supplementation increased the percentage of lesion formation when compared to untreated controls. The transgene decreased the number of lesions found in each aorta while leaving the total area of lesion formation unchanged suggesting that individual lesions are larger.

6) The mTIEhVAP-1 Transgene Inhibits Renal and Glomerular Hypertrophy while at the Same Time Promoting Glomerulosclerosis.

Glomerulosclerosis is the main renal lesion in human and experimental diabetes. Its pathogenesis is controversial and the role of renal and glomerular hypertrophy in the pathogenesis of glomerulosclerosis is unclear. In this study, the two renal pathologies were uncoupled.

Total kidney mass was decreased by the transgene. An atherogenic diet induced increase in kidney mass was also inhibited by the transgene. Morphometric analysis further revealed a significant transgene specific reduction of total glomeruli surface areas and an inhibition of atherogenic diet induced glomerular hypertrophy.

In contrast, histological analysis of kidney sections revealed glomerulosclerosis (decreased capillary space, increased cell number, increased extracellular matrix, and a thicker glomerular stalk) in transgenic mice fed the atherogenic diet. Mild glomerular lesions were also found in non-transgenic mice fed the atherogenic diet but to a lesser extent than in the transgenic mice. In addition, occasional glomerular cysts were present in the transgenic mice fed the atherogenic diet but were not present in the similarly fed non-transgenic mice.

CONCLUSIONS AND SIGNIFICANCE

Previous work has shown that SSAO activity is elevated in the serum of patients with congestive heart failure and specific inflammatory liver diseases. In this comprehensive study we for the first time show in vivo data indicating that this elevation of SSAO is not just a benign byproduct of the various disease states but that it is a cause of physiological and pathological changes. By performing these experiments in transgenic mice we reveal the consequences of increased SSAO without the additional complications of the disease states in which elevated SSAO is normally found.

We suggest that these changes result from the end products of SSAO substrate metabolism: hydrogen peroxide, ammonia, and aldehyde. On the one hand hydrogen peroxide can produce insulin-like effects that may be important for both obesity (lipogenesis promotion and lipolysis inhibition) and metabolic syndrome (increased glucose uptake) and on the other hand hydrogen peroxide is a key reactive oxygen species (ROS) that is implicated in endothelial cell toxicity and cardiovascular pathology. In addition, ammonia and formaldehyde are extremely reactive and cytotoxic chemicals that can promote aberrant, non-enzymatic glycation of proteins and may either directly or subsequently contribute to the late complications of diabetes such as hypertension, atherosclerosis and nephropathy.

Although these findings appear diametrically opposed they are not mutually exclusive. We propose that VAP-1 activity may be increased in metabolic syndrome as an attempt to regulate blood glucose levels and that vascular damage is subsequently promoted as a secondary consequence of this chronic enzyme activity. This suggests that manipulation of VAP-1 has potential to serve as a therapeutic treatment in conditions related to metabolic syndrome.

EXPERIMENTS

Reference to FIGS. 1A-1D:

Human VAP-1 over-expression and methylamine supplementation enhance glucose tolerance. The increases in blood glucose over fasting blood glucose levels at 30, 60, 90, and 120 minutes after glucose challenge (2.0 g IP glucose/kg body weight) are expressed as mean+SEM. (A) Glucose challenge of 26 week old non-transgenic (open symbols) and mTIEhVAP-1 transgenic mice (filled symbols) with normal tap water (solid lines) or with methylamine supplemented water (dashed lines). Significant effects on the rate of glucose clearance were identified by comparing the areas under the curve (AUC) of individual mice with an ANOVA (methylamine $p=0.0002$ and methylamine/transgene interaction $p=0.046$) and by comparing glucose levels at individual time points with unpaired Student's t-tests (asterisks, $p<0.01$ versus non-transgenic mice with normal water; crosses, $p<0.02$ versus non-transgenic mice with methylamine). (B) Glucose challenge of 10-12 week old transgenic mice with normal tap water (solid line) followed by 16 days of treatment with methylamine supplemented water (squares and dashed lines), and methylamine supplemented water as well as SSAO inhibitor injections (triangles and dashed lines). Significant effects were identified with paired Student's t-tests at individual time points (asterisks, $p<0.01$ and cross, $p=0.037$ versus transgenic mice with normal water) and for the AUC (normal water vs. methylamine treated, $p=0.006$; methylamine treated vs. methylamine treated plus SSAO inhibitor, $p=0.0005$; normal water vs. methylamine treated plus SSAO inhibitor, $p=0.0008$). (C) The mean±SEM percent of glycosylated hemoglobin (HbAlc) was determined from the blood of fasted, 57-59 week old non-transgenic (white bars) and transgenic (black bars) mice with (gray strips) or without oral methylamine supplementation. Significant effects on HbAlc levels were found with a mixed model ANOVA (transgene $p=0.03$ and methylamine supplementation $p<0.0001$), and a transgene/methylamine interaction was identified ($p=0.01$). Asterisks, unpaired students t-tests, $p<0.01$ verses non-transgenic mice with normal food and drink. (D) Glucose transport activity of muscles from non-transgenic and mTIEhVAP-1 transgenic mice. The soleus muscles from non-transgenic (NT, white bars) and transgenic (TG, black bars) mice with (gray strips) or without oral methylamine supplementation for 14 days were used for measurement of basal and insulin-stimulated rates of $2\text{-}[1\text{-}^{14}C]$-deoxy-D-glucose transport. Values are represented as the mean±SEM of the fold increase in transport compared to basal transport in non-transgenic mice with no treatment. Asterisks, $p<0.05$ vs. basal non-transgenic samples. Cross, significant difference when compared to non-transgenic mice with insulin alone ($p=0.02$) or non-transgenic mice with insulin plus methylamine ($p=0.01$).

Reference to FIGS. 2A-2B:

(A) The SSAO reaction product, formaldehyde, promotes AGE formation in vitro. The AGE-specific fluorescence spectra (ex 360/em 465) of protein samples (20 mg/ml RNase) incubated at 37° C. with or without 0.5 M glucose and 0.008% formaldehyde was periodically measured for 11 days. AU, arbitrary units. (B) The mTIEhVAP-1 transgene increases AGE-peptide levels in the sera of 64 week old mice. The AGE-specific fluorescence spectra (ex 360/em 465) of non-transgenic (NT, open bars) and transgenic (TG, solid bars) mice after chronic feeding with normal food (chow) and water (tap), methylamine supplemented water (Methyl.), or an atherogenic diet (athero.). A significant increase in AGE-specific fluorescence was found with the transgene when analyzing all of the treatments together (ANOVA, transgene effect $p=0.05$) and when analyzing the mice with just normal food and water (asterisk, unpaired students t-test, $p=0.05$). AU, arbitrary units.

We propose that SSAO activity is increased in diabetes as an attempt to regulate blood glucose levels and that vascular complications are subsequently promoted as a secondary consequence of chronic SSAO activity. When the in vivo levels of VAP-1 are increased the potential for SSAO activity is increased. The deamination of primary amines, such as methylamine, by VAP-1 produces the biologically active compounds hydrogen peroxide, ammonia, and aldehyde.

These compounds in turn can produce beneficial insulin-like effects while at the same time promoting AGE formation and vascular damage.

Vitamin B1 and its Metabolites as VAP-1 Inhibitors:

Fluorometric Detection of SSAO-mediated $H_2O_2$ Formation:

SSAO activity of the cells was measured using Amplex Red reagent (10-acetyl-3,7-dihydroxyphenoxazine; Molecular Probes Europe BV), a highly sensitive and stable probe for $H_2O_2$. Cultured cells (VAP-1 transfected CHO cells and their mock transfected controls) were rinsed with Krebs Ringer phosphate glucose (KRPG; 145 mM NaCl, 5.7 mM sodium phosphate, 4.86 mM KCl, 0.54 mM $CaCl_2$, 1.22 mM $MgSO_4$, 5.5 mM glucose, pH 7.35) and pre-incubated 30 min at 37° C. in 200 µl KRPG containing thiamine, penicillin or ampicillin (1 mg/ml). Catalytic reaction was initiated by addition of benzylamine as substrates and $H_2O_2$-detecting mixture containing horseradish peroxidase (final concentration 0.8 U/ml) and Amplex Red reagent (60 µM). The plates were incubated for 1-2 hours at 37° C. in the final volume of 250 µl, the bathing medium was clarified by centrifugation and placed in aliquots (200 µl) into white non-phosphorescent microplates (Cliniplate). Fluorescence intensity of the samples was measured (excitation, 545 nm; emission, 590 nm; Tecan ULTRA fluoropolarometer) and $H_2O_2$ concentration was calculated from calibration curves generated by serial dilutions of either standard $H_2O_2$ or resorufin, the product of the Amplex Red reaction (Molecular Probes).

Radiochemical Measurements of Monoamine Oxidase Activity

Amine oxidase activity was assayed radiochemically using [7-$^{14}$C]-benzylamine hydrochloride (spec. act. 57 mCi/mmol, Amersham) as a substrate and 25 microliters of serum. The reaction was initiated by addition of 6 µmol/L [$^{14}$C]-benzylamine (40000 dpm) and terminated after 1 hour by citric acid. The aldehydes were extracted into toluene containing diphenyloxazole and the formation of [$^{14}$C]-labelled benzaldehyde was quantified by scintillation counting. Potential inhibition of serum VAP-1/SSAO enzymatic activity was measured in presence of indicated concentrations of thiamine. Finally, enzymatic activity of serum VAP-1/SSAO of six volunteers was measured before and after eating vitamin B1 100 mg/day for 5 to 9 days. Similarly serum VAP-1/SSAO activity of four volunteers eating benfothiamine 200 mg/day for four days was measured.

Results

The inhibitory percentages obtained with thiamine after treating VAP-1 transfected CHO cells in fluorometric assays are listed in Table 1. Controls, penicillin and ampicillin, did not inhibit the activity. In vitro thiamine decreased serum VAP-1/SSAO activity as follows: 1 mg/ml, 87%; 800 micrograms/ml, 70%; 400 micrograms/ml 39%; 200 micrograms/ml 32%. In vivo response of VAP-1/SSAO enzymatic activity to vitamin B1 varied between individuals. Four of the six volunteers responded to vitamin B. Their VAP-1 enzyme activity at the end of the experiment had decreased: 25, 2, 32 and 16% (mean 19%). Although the benfothiamine dose was low and it was eaten only for four days, it decreased SSAO activity of each individual (9, 24, 8 and 27%).

TABLE 1

Thiamine inhibits SSAO activity of VAP-1 transfected cells in a dose dependent manner

| Thiamine dose (µg/ml) | Inhibition % |
|---|---|
| 500 | 61.5 ± 2.5 |
| 375 | 47.0 ± 9.0 |
| 250 | 42.0 ± 2.0 |
| 175 | 35.5 ± 2.5 |
| 125 | 26.5 ± 11.0 |
| 63 | 10.5 ± 8.5 |

Figure 3:
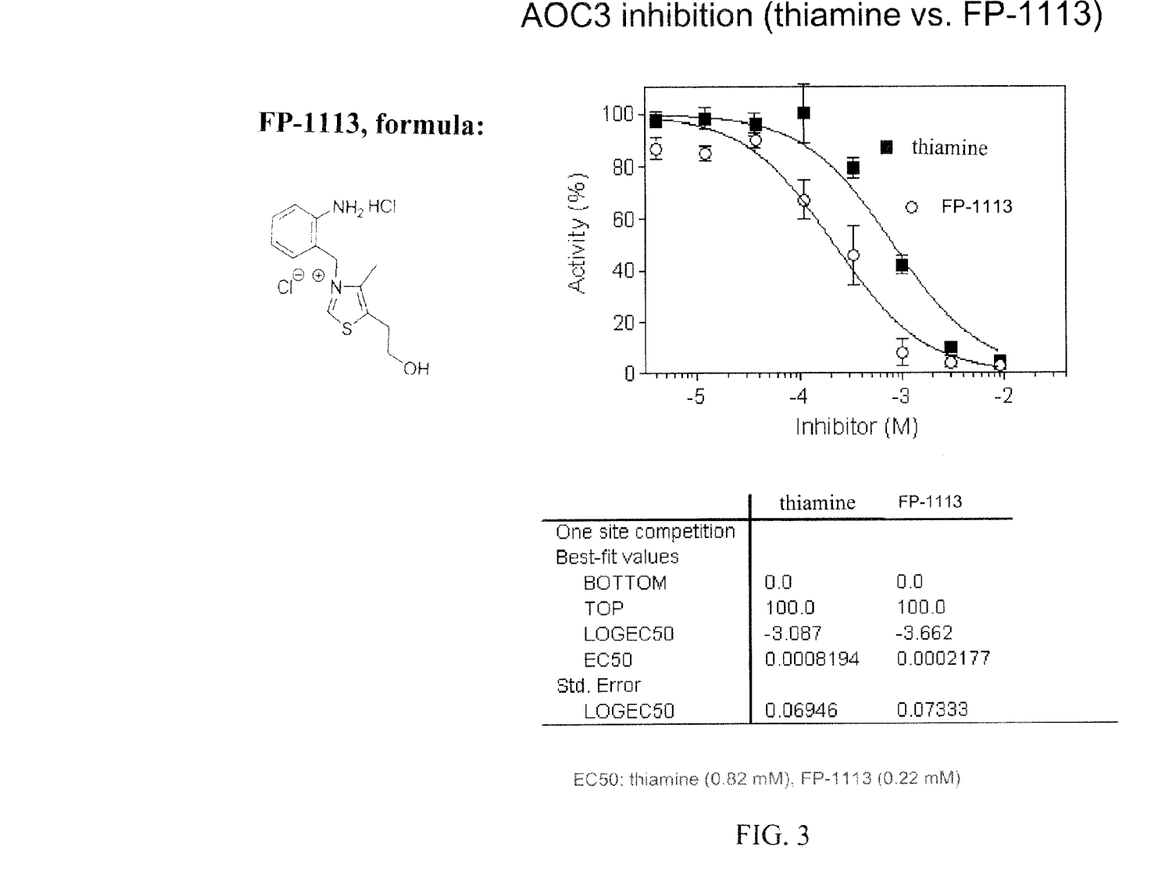
FIG. 3 shows the structure of 3-(2-aminobenzyl)-5-(2-hydroxyethyl)-4-methyl-thiazolium chloride hydrochloride as well as the amine oxidase, copper containing 3 (AOC3) inhibiting effect of this compound and thiamine.

The Vitamin B1 Derivative 3-(2-aminobenzyl)-5-(2-hydroxyethyl)-4-methyl-thiazolium Chloride Hydrochloride (FP-1113) as Inhibitor of SSAO Activity The enzyme inhibiting activity was tested as described above. The results are shown in FIG. 3. It can be seen that FP-1113 is a stronger SSAO-inhibitor than thiamine.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

The invention claimed is:

1. A method of ameliorating or alleviating metabolic syndrome in an individual in need thereof, said method comprising administering a therapeutically effective amount of a vascular adhesion protein 1 (VAP-1) semicarbazide-sensitive amine oxidase (SSAO) enzyme inhibitor selected from the group consisting of vitamin B1, its derivative 3-(2-aminobenzyl)-5-(2-hydroxyethyl)-4-methyl-thiazolium chloride hydrochloride, and its precursor benfotiamine to said individual, wherein said metabolic syndrome is characterized by (a) central obesity as measured by waist circumference greater than 102 cm for males and greater than 88 cm for females and (b) two of the following: (i) fasting plasma glucose greater than 6.1 mmol/l, (ii) blood triglycerides greater than 1.7 mmol/l, (iii) blood HDL cholesterol less than 1.03 mmol/l for males and less than 1.29 mmol/l for females and (iv) blood pressure greater than 130/85 mm Hg.

2. The method according to claim 1, wherein said metabolic syndrome has caused in said individual a disease or condition selected from the group consisting of atherosclerosis, vascular retinopathies, retinopathy, glomerulosclerosis, nephropathy, nephrotic syndrome, polyneuropathy, mononeuropathies, autonomic neuropathy, glaucoma, grey cataract, foot ulcers, and joint problems.

3. The method according to claim 1 wherein the amine oxidase enzyme inhibitor is vitamin B1.

4. The method according to claim 1 wherein the amine oxidase enzyme inhibitor is the vitamin B1 precursor benfotiamine.

5. The method according to claim 1, wherein the amine oxidase enzyme inhibitor is the vitamin B1 derivative 3-(2-aminobenzyl)-5-(2-hydroxyethyl)-4-methyl-thiazolium chloride hydrochloride.

* * * * *